(12) United States Patent
Proett et al.

(10) Patent No.: US 7,021,405 B2
(45) Date of Patent: Apr. 4, 2006

(54) DETERMINING GRADIENTS USING A MULTI-PROBED FORMATION TESTER

(75) Inventors: Mark A. Proett, Houston, TX (US); Gregory N. Gilbert, Sugar Land, TX (US); David E. Ball, Stafford, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 24 days.

(21) Appl. No.: 10/837,764

(22) Filed: May 3, 2004

(65) Prior Publication Data

US 2004/0230378 A1    Nov. 18, 2004

Related U.S. Application Data

(60) Provisional application No. 60/467,329, filed on May 2, 2003.

(51) Int. Cl.
*G06F 19/00* (2006.01)

(52) U.S. Cl. ............................... 175/65; 73/155; 702/1

(58) Field of Classification Search ............. 702/1–14; 73/155, 152.05; 166/358, 264; 175/65, 175/40; 703/10, 5
See application file for complete search history.

(56) References Cited

U.S. PATENT DOCUMENTS

| 4,860,580 A | 8/1989 | DuRocher ..................... 73/155 |
| 4,860,581 A | 8/1989 | Zimmerman et al. ......... 73/155 |
| 4,936,139 A | 6/1990 | Zimmerman et al. ......... 73/155 |
| 5,247,830 A | 9/1993 | Goode .......................... 73/155 |
| 5,622,223 A * | 4/1997 | Vasquez ...................... 166/264 |
| 5,703,286 A | 12/1997 | Proett et al. ............. 73/152.05 |
| 6,176,323 B1 * | 1/2001 | Weirich et al. ............... 175/40 |
| 6,498,989 B1 * | 12/2002 | Pisetski et al. ............... 702/14 |
| 6,609,067 B1 * | 8/2003 | Tare et al. ...................... 702/9 |
| 6,826,486 B1 * | 11/2004 | Malinverno .................. 702/16 |
| 6,832,158 B1 * | 12/2004 | Mese et al. ..................... 702/9 |
| 2003/0094040 A1 | 5/2003 | Proett et al. ............. 73/152.05 |
| 2003/0098181 A1 * | 5/2003 | Aronstam et al. ............ 175/65 |
| 2004/0065440 A1 * | 4/2004 | Farabee et al. ............. 166/358 |

FOREIGN PATENT DOCUMENTS

WO    WO 2004/099552 A2 *    5/2004

OTHER PUBLICATIONS

Goode et al., "Analytic Models for a Multiple Probe Formation Tester," Society of Petroleum Engineers Conference, Paper SPE 20737, 22 pages (1990).

(Continued)

*Primary Examiner*—Bryan Bui
*Assistant Examiner*—Victor J. Taylor
(74) *Attorney, Agent, or Firm*—Conley Rose, P.C.

(57) ABSTRACT

Methods for operating multi-probed formation testers to determine a fluid density gradient in the formation. The probes of the multi-probed formation tester are connected to a pressure gauge through a flowline that establishes a differential height between the probes. In some embodiments, a gradient of the fluid density in the flowline is determined as a function of the gradient of fluid density in the wellbore. The flowline fluid density gradient is then used to determine a formation fluid density gradient as a function of the flowline fluid density gradient.

23 Claims, 4 Drawing Sheets

OTHER PUBLICATIONS

Goode et al., "Multiple-Probe Formation Testing and Vertical Reservoir Continuity," Society of Petroleum Engineers Conference, Paper SPE 22738, pp. 787-800 (1991).

Goode et al., "Influence of an Invaded Zone on a Multiple Probe Formation Tester," Society of Petroleum Engineers Conference, Paper SPE 23030, 13 pages (1991).

* cited by examiner

DETERMINING GRADIENTS USING A MULTI-PROBED FORMATION TESTER

CROSS-REFERENCE TO RELATED APPLICATIONS

This application claims priority to U.S. Provisional Patent Application 60/467,329, filed May 2, 2003, and entitled "Determining Gradients using a Multi-probed Formation Tester," which is hereby incorporated by reference herein for all purposes.

STATEMENT REGARDING FEDERALLY SPONSORED RESEARCH OR DEVELOPMENT

Not applicable.

BACKGROUND OF THE INVENTION

The embodiments of the present invention relate generally to methods for determining pressure gradients in a wellbore. More specifically, the embodiments relate to methods for determining formation pressure gradients using multiple pressure readings from different depths in the wellbore.

Due to the high costs associated with drilling and producing hydrocarbon wells, optimizing the performance of wells has become very important. The acquisition of accurate data from the wellbore is critical to the optimization of the completion, production and/or rework of hydrocarbon wells. This wellbore data can be used to determine the location and quality of hydrocarbon reserves, whether the reserves can be produced through the wellbore, and for well control during drilling operations.

Well logging is a means of gathering data from subsurface formations by suspending measuring instruments within a wellbore and raising or lowering the instruments while measurements are made along the length of the wellbore. For example, data may be collected by lowering a measuring instrument into the wellbore using wireline logging, logging-while-drilling (LWD), or measurement-while-drilling (MWD) equipment. In wireline logging operations, the drill string is removed from the wellbore and measurement tools are lowered into the wellbore using a heavy cable that includes wires for providing power and control from the surface. In LWD and MWD operations, the measurement tools are integrated into the drill string and are ordinarily powered by batteries and controlled by either on-board and/or remote control systems. Regardless of the type of logging equipment used, the measurement tools normally acquire data from multiple depths along the length of the well. This data is processed to provide an informational picture, or log, of the formation, which is then used to, among other things, determine the location and quality of hydrocarbon reserves. One such measurement tool used to evaluate subsurface formations is a formation tester.

To understand the mechanics of formation testing, it is important to first understand how hydrocarbons are stored in subterranean formations. Hydrocarbons are not typically located in large underground pools, but are instead found within very small holes, or pore spaces, within certain types of rock. The ability of a rock formation to allow hydrocarbons to move between the pores, and consequently into a wellbore, is known as permeability. The viscosity of the oil is also an important parameter and the permeability divided by the viscosity is termed "mobility" ($k/\mu$). Similarly, the hydrocarbons contained within these formations are usually under pressure and it is important to determine the magnitude of that pressure in order to safely and efficiently produce the well.

During drilling operations, a wellbore is typically filled with a drilling fluid ("mud"), such as water, or a water-based or oil-based mud. The density of the drilling fluid can be increased by adding special solids that are suspended in the mud. Increasing the density of the drilling fluid increases the hydrostatic pressure that helps maintain the integrity of the wellbore and prevents unwanted formation fluids from entering the wellbore. The drilling fluid is continuously circulated during drilling operations. Over time, as some of the liquid portion of the mud flows into the formation, solids in the mud are deposited on the inner wall of the wellbore to form a mudcake.

The mudcake acts as a membrane between the wellbore, which is filled with drilling fluid, and the hydrocarbon formation. The mudcake also limits the migration of drilling fluids from the area of high hydrostatic pressure in the wellbore to the relatively low-pressure formation. Mudcakes typically range from about 0.25 to 0.5 inch thick, and polymeric mudcakes are often about 0.1 inch thick. On the formation side of the mudcake, the pressure gradually decreases to equalize with the pressure of the surrounding formation.

In a typical formation testing operation, a formation tester is lowered to a desired depth within a wellbore. The wellbore is filled with mud, and the wall of the wellbore is coated with a mudcake. Because the inside of the tool is open to the well, hydrostatic pressure inside and outside the tool are equal. Once the formation tester is at the desired depth, a probe is extended to sealingly engage the wall of the wellbore and the tester internal flowline is isolated from the wellbore by closing one or more equalizer valves.

After the probe is extended and the flowline isolated, a small cylinder that is in communication with the flowline is drawn back to increase the total flowline volume. This causes the pressure within the flowline to decrease substantially below formation pressure. Then fluid contained within the pore space of the rock adjacent to the probe is drawn into the flowline of the tool and the pressure increases to nearly formation pressure. The formation tester flowline in then in fluid communication with the formation and a pressure sensor can monitor the pressure of fluid in flowline over time. This process is known as a pretest. From this pressure versus time data, the pressure and permeability of the formation can be determined. Techniques for determining the pressure and permeability of the formation from the pressure versus time data are discussed in U.S. Pat. No. 5,703,286, issued to Proett et al., and incorporated herein by reference for all purposes.

Determining an accurate formation gradient is another one of the principle applications for formation testers. Methods for determining the formation gradient have performed several formation tests at different depths within the well. These methods often involve relocating the testing tool several times during the procedure. It has been proposed that by using a multi-probed tester with at least two widely spaced probes an improved formation gradient can be obtained at a single testing depth.

The primary advantage to using a multi-probed tester is that by using the fixed distance between the probes the accuracy could be improved, reducing the number of tool movements and potentially saving rig time. This method of multi-probed testing is not as straightforward as it might appear. One method of multi-probed testing is discussed in U.S. Pat. No. 4,860,580, issued to DuRocher, which is hereby incorporated by reference herein for all purposes. Other multi-probed formation testing methods are described in co-owned pending U.S. patent application Ser. No. 10/254,310, which is hereby incorporated by reference herein for all purposes.

In formation testing, the pressure gauge (typically a high accuracy quartz gauge) measures the pressure from the probes plus the pressure differential from the probe to the gauge. This pressure differential is related to fluid density of the fluid in the flowline. In conventional, single probe testing it is assumed that the effect of tester flowline density on pressure readings can be neglected because the flowline density does not change between pressure tests.

Now consider two probes spaced more than 10 ft apart. In this case, there is a different pressure differential for each probe due to the flowline fluid density and each probe spacing. Because one probe is a significantly greater distance from the pressure gauge, the differential pressure effect on each probe is significantly different. If this effect is not accounted for, the gradient determined by the multi-probed measurement will need to be corrected.

Thus, there remains a need in the art for methods of performing multi-probed formation testing that take into account the change in differential pressure due to the distance between the probes. Therefore, the embodiments of the present invention are directed to methods for calculating pressure gradients in multi-probed formation testers that seek to overcome the limitations of the prior art.

SUMMARY OF THE PREFERRED EMBODIMENTS

Embodiments of the invention include methods for operating multi-probed formation testers to determine a fluid density gradient in the formation. The probes of the multi-probed formation tester are connected to a pressure gauge through a flowline that establishes a differential height between the probes. In some embodiments, a gradient of the fluid density in the flowline is determined as a function of the gradient of fluid density in the wellbore. The flowline fluid density gradient is then used to determine a formation fluid density gradient as a function of the flowline fluid density gradient.

The preferred embodiments provide methods for calculating pressure gradients in multi-probed formation testers that compensate for flowline differential pressure created by varying distances between the tester probes and the pressure sensors. One method includes determining the wellbore gradient by taking a pressure measurement from the wellbore from two pressure ports in the flowline at different depths on the same tool. Pressure measurements are taken from each probe while the probe being sampled is isolated from other probes. The formation pressure can then be determined and corrected for the differential pressure effect from the flowline.

The methods described herein can be adapted for use in any fluid sampling tool. For purposes of discussion one exemplary tool will be described, where that tool includes two dual probe sections (DPS) and one quartz gauge section (QGS). Each DPS includes two probes, a port providing access to the wellbore, and strain gauge pressure sensors integrated into the DPS. A common flowline connects the two DPS's to the QGS. Exemplary DPS and QGS units are available as components of Halliburton's Reservoir Description Tool (RDT).

In a first operating mode the QGS is used for the formation gradient determination. The wellbore gradient, or mud density, can be determined using the QGS to take pressure measurements through one of the DPS ports at two depths in the wellbore. The flowline gradient can be determined by taking a pressure measurement, using the QGS, through each of the DPS ports with the tool at a single location. The probes can then be set and the QGS is used to measure the pressure at each probe, when the flowline to the probe being measured is isolated from the other probes.

In the second mode, strain gauges located at fixed distances from the probes are calibrated using the QGS and the formation gradient is determined using the strain gauges. This method is similar to the QGS-only method but the flowline density, as determined before each pressure test is started, is used to offset the strain gauge measurements. Thus, the strain gauges can be used to determine the formation gradient and monitor changes in the flowline density. The flowline density may be rechecked following a formation pressure test to determine accuracy of the measurements and/or contamination of the fluid sample.

A multi-probe tester also allows enough separate measurements of formation, wellbore, and flowline pressure to enable meaningful statistical analysis of the pressure test measurements. This statistical analysis may provide indication of problems in data acquisition or a malfunction of the testing tool.

Thus, the present invention comprises a combination of features and advantages that enable it to provide efficient, accurate determination of formation pressure. These and various other characteristics and advantages of the preferred embodiments will be readily apparent to those skilled in the art upon reading the following detailed description and by referring to the accompanying drawings.

BRIEF DESCRIPTION OF THE DRAWINGS

For a more detailed understanding of the preferred embodiments, reference is made to the accompanying Figures, wherein.

DETAILED DESCRIPTION OF THE PREFERRED EMBODIMENTS

Figure 1:
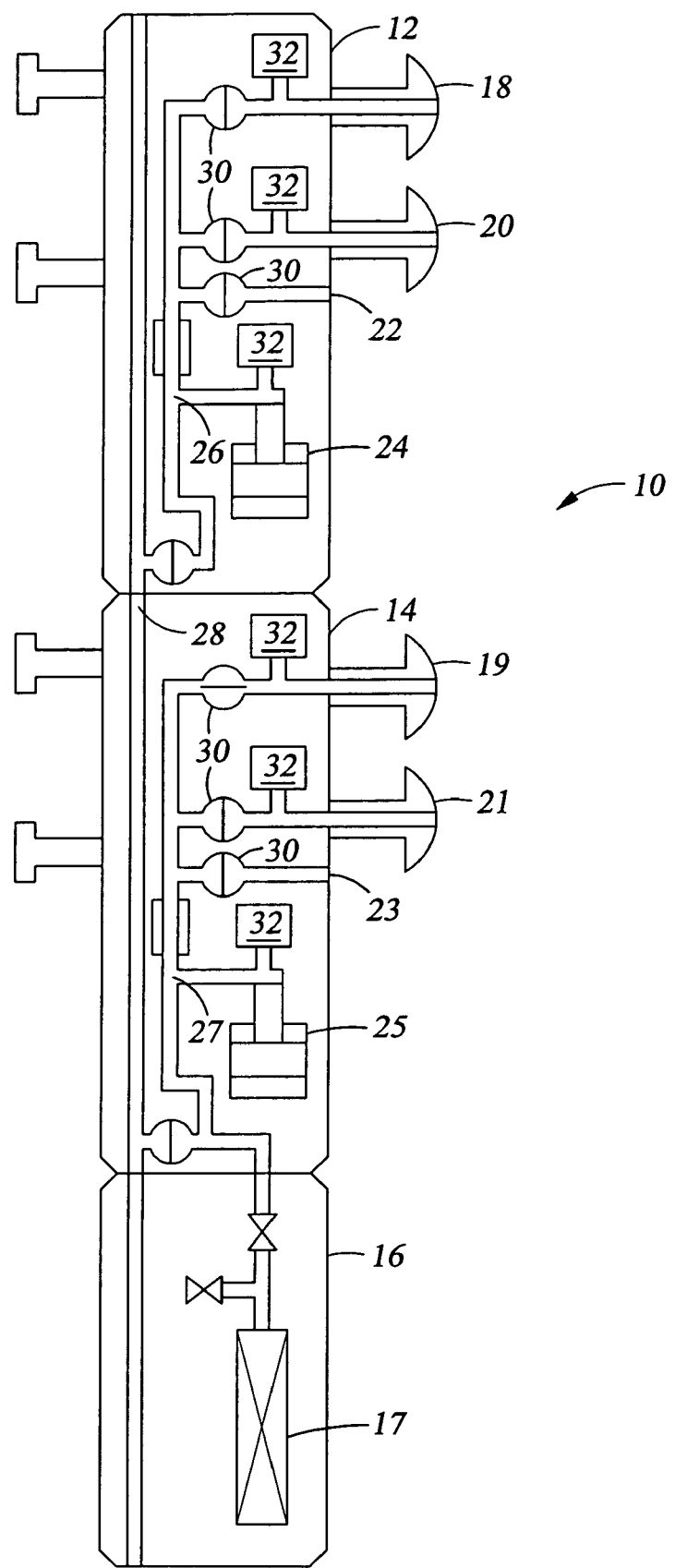
FIG. 1 is a schematic view of a reservoir description tool.

In the description that follows, like parts are marked throughout the specification and drawings with the same reference numerals, respectively. The drawing figures are not necessarily to scale. Certain features of the invention may be shown exaggerated in scale or in somewhat schematic form and some details of conventional elements may not be shown in the interest of clarity and conciseness. The present invention is susceptible to embodiments of different forms. There are shown in the drawings, and herein will be described in detail, specific embodiments of the present invention with the understanding that the present disclosure is to be considered an exemplification of the principles of the invention, and is not intended to limit the invention to that illustrated and described herein. It is to be fully recognized that the different teachings of the embodiments discussed below may be employed separately or in any suitable combination to produce the desired results.

In particular, various embodiments of the present invention provide a number of different methods for measuring formation gradients using multi-probed formation testing tools. The concepts of the invention are discussed in the context of a reservoir description tool having two dual-probe testing sections and a single quartz pressure gauge, but the use of the concepts of the present invention is not limited to this particular application and may be applied to downhole pressure testing application. The concepts disclosed herein may find application with other multi-probe formation testing assemblies and wellbore pressure sensors, as well as other applications to which the concepts of the current invention may be applied.

Referring now to FIG. 1, a schematic view of a formation testing tool 10 is shown including an upper dual probe section (DPS) 12, a lower DPS 14, and a quartz gauge section (QGS) 16. QGS 16 includes a quartz pressure gauge 17. Each DPS has an upper probe 18, 19, a lower probe 20, 21, a port 22, 23, and a pretest piston 24, 25. These components are interconnected by a private flowline 26,27 that is connected to a common flowline 28 provides fluid communication between the two DPS sections 12, 14 and the QGS 16. Valves 30 control the movement of fluid within and between the components. Strain gauge pressure sensors 32 are provided to measure the pressure at several locations within tool 10.

In general, the determination of formation density (lb/in3) involves the measurement of the pressure gradient (psi/ft) in the wellbore, the flowline, and the formation. These three distinct measurement steps are not always performed in any distinct order and may be alternated or re-measured during the course of a testing procedure. For the purposes of this discussion, and in reference to FIG. 7, we will analyze a procedure where the first step is measuring wellbore gradient (mud density) 52, the second step is measuring flowline gradient 54, and the final step is measuring formation gradient 56.

Figure 2:
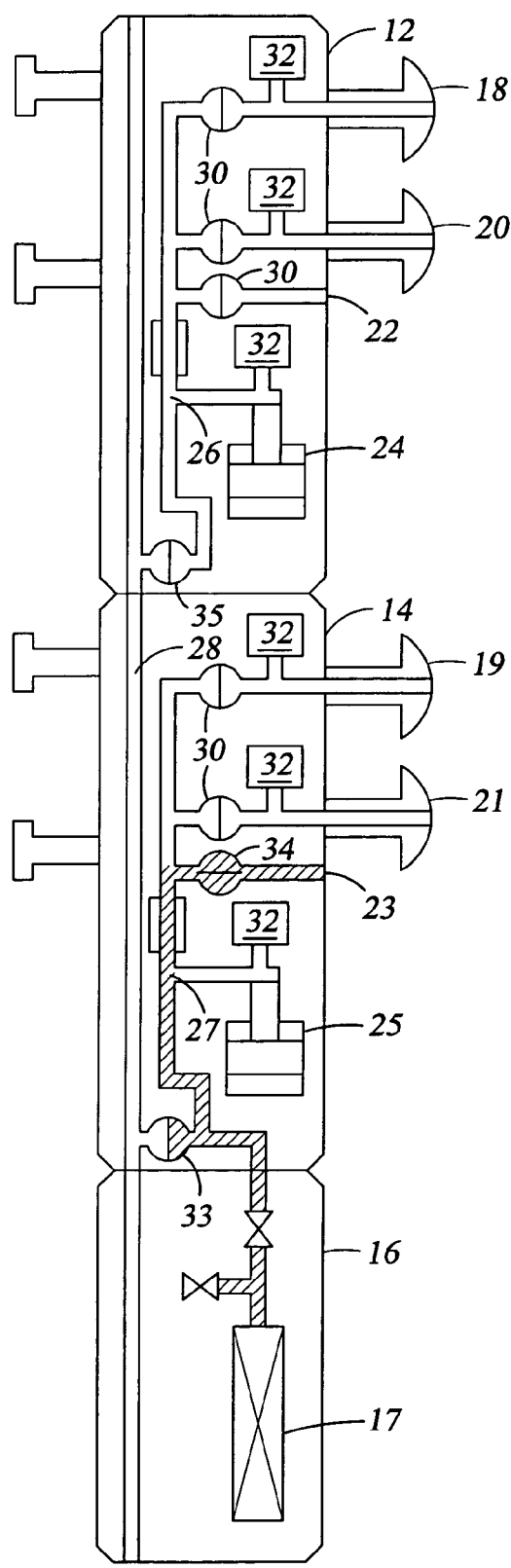
FIG. 2 is a schematic view of the tool of FIG. 1 in a wellbore gradient and first flowline gradient testing mode.

Referring now to FIG. 2, the tool 10 of FIG. 1 is shown in a position to test wellbore gradient. Although the wellbore gradient is dependent on the mud density, which is often known, it may be desirable to verify the wellbore gradient within the depths of interest for the test. The wellbore gradient can be determined using the QGS 16 to take a pressure measurement through DPS port 23 (alternatively port 22 could be used) at two different depths. A valve 34, opens port 23 to the wellbore, placing QGS 16 in fluid communication with the wellbore fluid. Measuring the pressure at two different depths and knowing the distance between these two depths allows the wellbore gradient to be determined by:

$$\rho_m = \frac{P_{D2} - P_{D1}}{D1 - D2}; \tag{1}$$

wherein $\rho_m$ is the wellbore gradient (psi/ft), D1 is a first depth (ft), $P_{D1}$ is the pressure measured at the first depth (psi), D2 is a second depth (ft), and $P_{D2}$ is the pressure measured at the second depth (psi). The depth points are assumed to be a true vertical depth and not necessarily the distance into the well.

The assumption could be made that the flowline gradient (i.e., fluid density) is equal to the mud gradient. This may be the case if the flowlines are purged prior to testing, however, during pressure testing, formation fluid can be drawn into the flowlines and cause some errors in the formation gradient estimate. Thus, the following procedure can be used to determine the difference between the mud gradient and flowline gradient and any time before and after pressure testing through the DPS sections.

Figure 3:
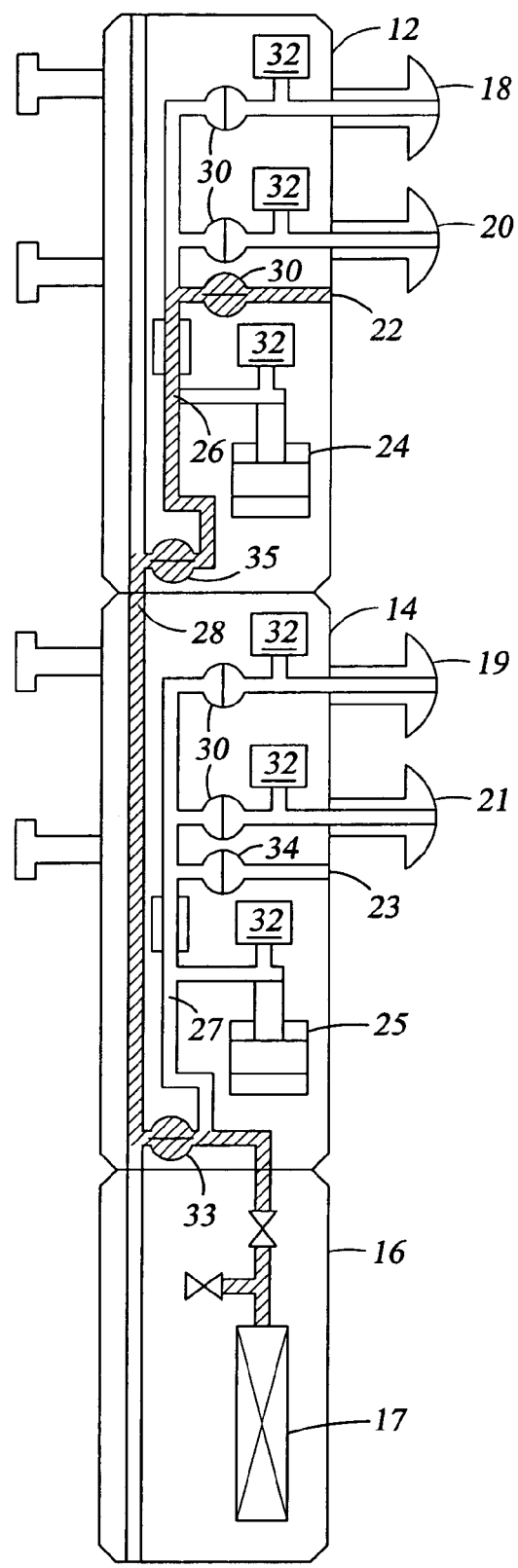
FIG. 3 is a schematic view of the tool of FIG. 1 in a second flowline gradient testing mode

As shown in FIG. 2, the wellbore pressure can be measured through the lower DPS section 14 at any time when the upper DPS flowline valve 35 is closed so that the lower DPS section 14 is isolated. Once the wellbore pressure is measured through the lower DPS 14, the wellbore pressure through the upper DPS 12 can be measured by setting the lower DPS 14, closing the probe valves 34, and opening the upper DPS flowline valve 35, as shown in FIG. 3.

Referring back to FIG. 2, the actual pressure at port 23, $P_{eq1}$ is equal to the depth of the tool, TVD, times the wellbore gradient, $\rho_m$; or $$P_{eq1} = \rho_m TVD. \tag{2}$$

The pressure measured by quartz gauge 17 is the actual pressure at port 23 plus the added differential pressure of the fluid column in flowline 27 between port 23 and the gauge. This measured pressure is represented by:

$$P_{qge1} = P_{eq1} + \rho_{fl} L_3 \cos(\theta_d); \tag{3}$$

where $P_{qge1}$ is the measured gauge pressure, $\rho_{fl}$ is the flowline gradient, $L_3$ is the distance between port 23 and gauge 17, and and $\theta_d$ is the dipping angle of the well.

Referring now to FIG. 3, the pressure at port 22, $P_{eq2}$, (relative to gauge 17) is equal to the actual pressure at port 23, $P_{eq1}$, plus the differential pressure from fluid in flowlines 26, 28; or $$P_{eq2} = P_{eq1} + \rho_m (L_4 - L_3) \cos(\theta_d); \tag{4}$$

where $L_4$ is the distance between port 22 and gauge 17. The pressure measured by quartz gauge 17 is the actual pressure at port 22 plus the added differential pressure of the fluid column in flowlines 26 and 28 between port 22 and the gauge. Thus, this measured pressure is represented by:

$$P_{qge2} = P_{eq2} + \rho_{fl} L_4 \cos(\theta_d); \tag{5}$$

where $P_{qge2}$ is the measured gauge pressure, $\rho_{fl}$ is the flowline gradient, and $L_4$ is the distance between port 22 and gauge 17.

Now the flowline density can be determined as follows:

$$\rho_{fl} = \rho_m + \frac{P_{qge2} - P_{qge1}}{\Delta L \cos(\theta_d)}; \tag{6}$$

wherein $\rho_{fl}$ is the flowline fluid density gradient (psi/ft), $\rho_m$ is the wellbore gradient (psi/ft), $P_{qgp1}$ is the quartz gauge measured through lower DPS probe (psi), $P_{qgp2}$ is the quartz gauge measured through the upper DPS probe (psi), $\Delta L$ ($L_4 - L_3$) is the spacing between upper and lower DPS probes (ft), and $\theta_d$ is the dip angle (deg).

Figure 4:
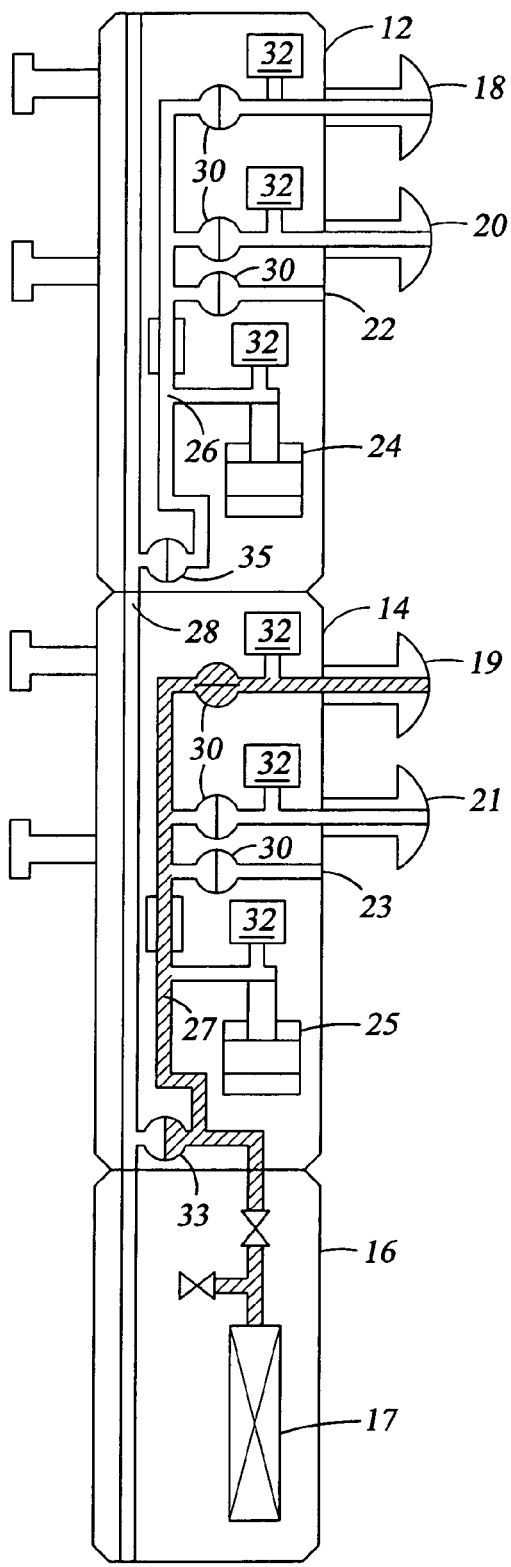
FIG. 4 is a schematic view of the tool of FIG. 1 in a first formation gradient testing mode.
Figure 5:
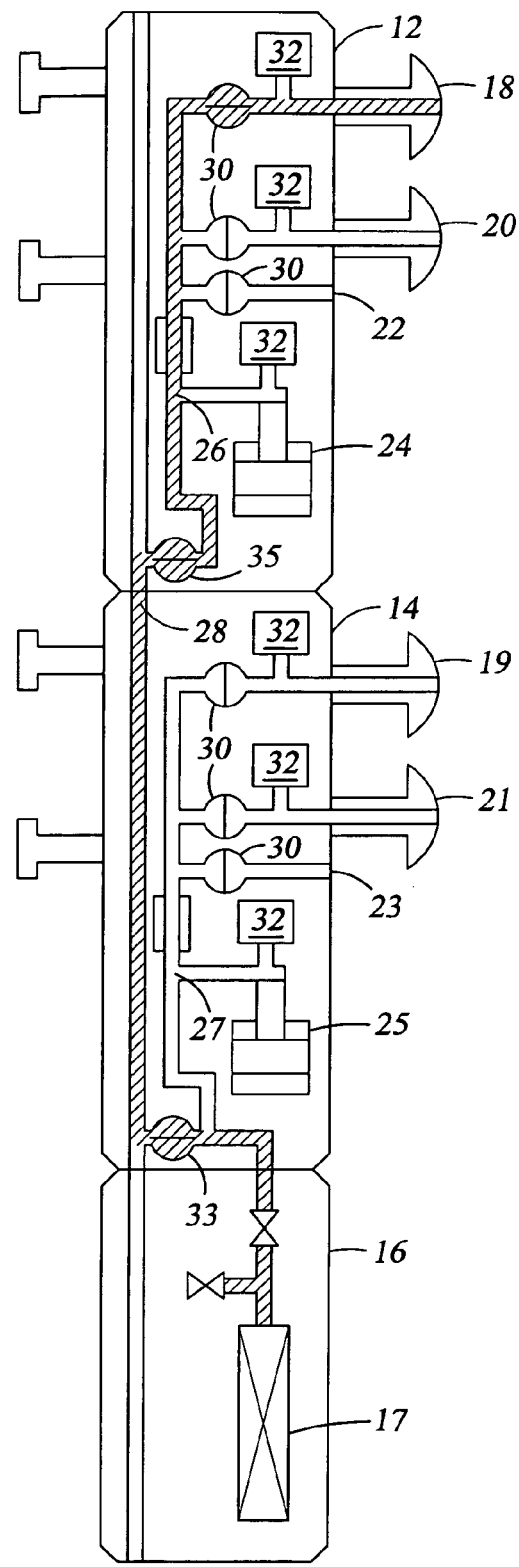
FIG. 5 is a schematic view of the tool of FIG. 1 in a second formation gradient testing mode.

Referring now to FIG. 4, the lower DPS 14 is in communication with QGS 16 through the DPS private flowline 27 so that pressure measurements at probe 19 can be taken by gauge 17. After a pressure measurement has been taken, lower probe valves 36 are closed and gauge 17 can then take pressure measurements from upper DPS probe 18 through flowlines 26 and 28, as shown in FIG. 5.

The pressures relative to the probe and quartz gauge are essentially the same as those for the ports as described above, except that the distances are between the probes as opposed to the ports. Assuming the flowline density is now known (by Equation 6) and is constant throughout the pressure testing the correction for the formation gradient can be determined by solving the simultaneous equations as follows:

$$P_{dp1} = \rho_f TVD; \quad (7)$$

$$P_{qgp1} = P_{dp1} + \rho_{fl} L_1 \cos(\theta_d); \quad (8)$$

$$P_{dp2} = P_{dp1} + \rho_f (L_2 - L_1)\cos(\theta_d); \quad (9)$$

$$P_{qgp2} = P_{dp2} + \rho_{fl} L_2 \cos(\theta_d); \text{ and} \quad (10)$$

$$\rho_f = \rho_{fl} - \frac{P_{qgp2} - P_{qgp1}}{\Delta L \cos(\theta_d)}; \quad (11)$$

where $\rho_f$ is the formation fluid density gradient (psi/ft), $\rho_{fl}$ is the flowline fluid density gradient (psi/ft), $P_{qgp1}$ is the quartz gauge measured through lower DPS probe 19 (psi), $P_{qgp2}$ is the quartz gauge measured through upper DPS probe 18 (psi), $L_1$ is the distance between probe 19 and gauge 17 (ft), $L_2$ is the distance between probe 18 and gauge 17 (ft), $\Delta L$ ($L_2-L_1$) is the spacing between upper and lower DPS probes (ft), and $\theta_d$ the dip angle (deg).

One of the disadvantages to a method using only QGS 16 for pressure measurements is that the flowline gradient can change while testing. Another disadvantage is that the public flowline 28 volume must be contended with when testing with the upper DPS section. This can cause delays in the buildup times particularly in low permeability zones (i.e., <10 md) where it may take significant time for formation fluid to fill the flowline.

Thus, a second method offers the opportunity to constantly check for flowline gradient changes and make constant corrections to the gradient estimated using strain gauges 32. One disadvantage to using strain gauges 32 is that they are less accurate than quartz gauge 17. While the strain gauges have good resolution (i.e., <0.10 psi), they have poor accuracy (i.e., >±5 psi). Thus, if strain gauges 32 can be offset from the quartz gauge 17 and the pressure measurements are taken with strain gauges 32, with tool 10 at the same depth point, then certain procedures can take advantage of the strain gauge resolutions while minimizing effects of their accuracy.

The procedure is identical to the QGS-only procedure described above with one exception. The flowline density is determined before starting the pressure testing (i.e., FIG. 2–3, Eq. 1–6) and then used to offset the strain gauge measurements done using a standard, real-time software strain gauge calibration option. Next, the probe pressure tests are performed as described previously but the individual probe strain gauges 32 can be used to determine the formation gradient without correction, assuming the other probes are isolated from the flowline.

The strain gauges 32 can also be used to monitor flowline density changes. After pressure testing is completed at a single depth point, the QGS determined gradients can be checked against the strain gauge gradients. Also, the quartz gauge 17 can be used to check the final flowline density and compared against the strain gauge determinations. The determination of flowline gradient can also be used to determine contamination of the acquired sample by comparing the flowline gradient to the formation gradient.

There are multiple ways of determining the formation gradient at a single testing depth. For example, pressure test measurements can be taken through each probe. These pressure test measurement are made using standard pressure testing techniques employed by formation testers for the purpose of measuring formation pressure. These tests are commonly called pretests. First, the quartz gauge measurement is made by opening the appropriate flowline valves to the quartz gauge. Then the strain gauge measurement can be made at the same time.

Figures 6, 7:
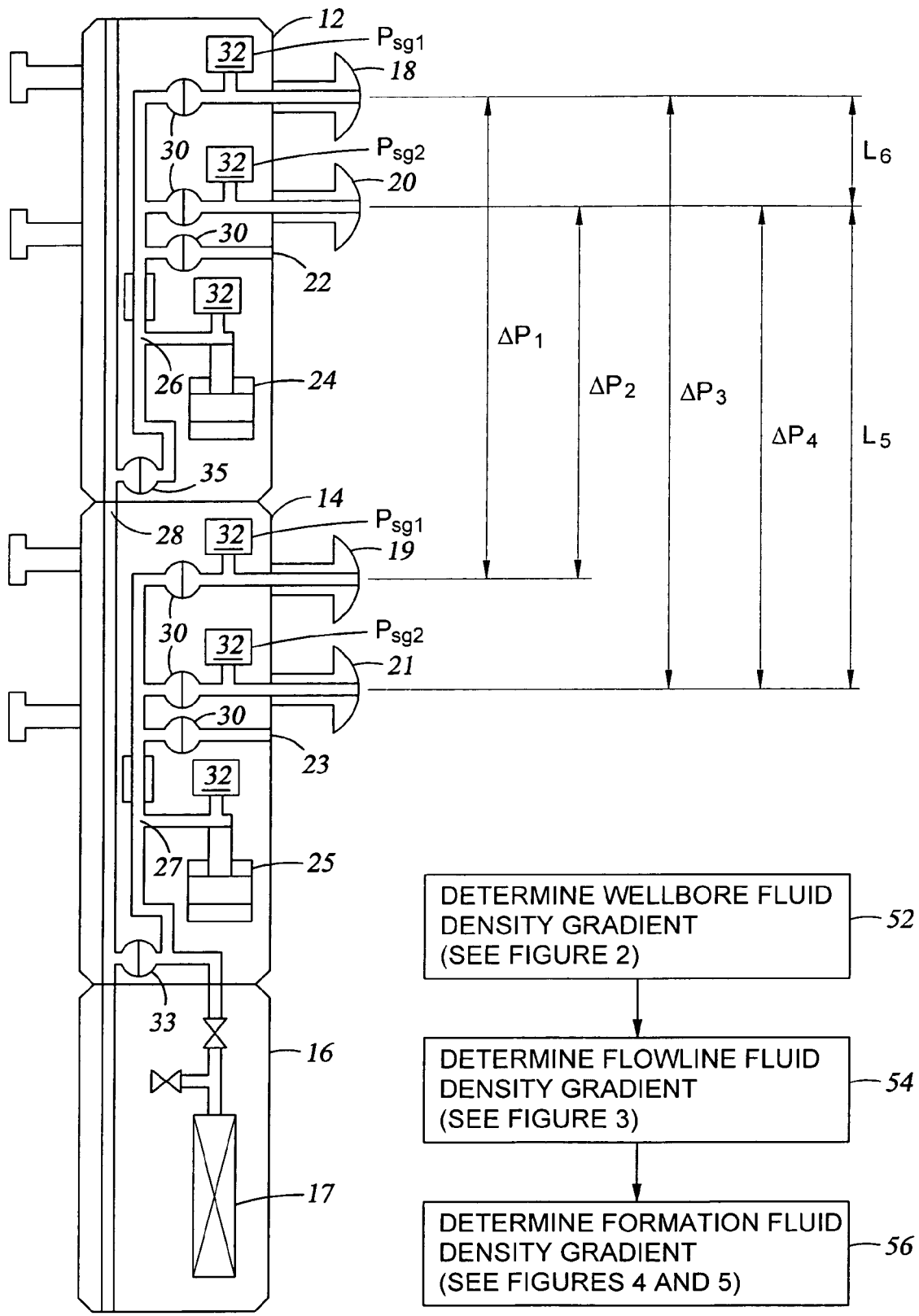
FIG. 6 is a schematic view of the tool of FIG. 1 illustrating the distances between probes.
FIG. 7 is a flow chart illustrating a method in accordance with the present invention.

Referring now to FIG. 6, where combinations of probe pressures differentials are illustrated. If all the pressure differentials are considered (with exception to $L_6$ short spacing) there are four separate ways to determine the formation gradient from either the strain or QGS gauges. This makes a total of eight different gradient estimates. All of these estimates can be combined and a statistical analysis and used to determine the mean and standard deviation of the gradient for each depth point. Furthermore, specific measurements can be eliminated if they deviate too far from the mean. For example, see Table 1 below where the formation pretest pressure measurements are:

$P_{qg1}$ is the probe 18 quartz gauge formation pressure(psi)
$P_{sg1}$ is the probe 18 strain gauge formation pressure(psi)
$P_{qg2}$ is the probe 20 quartz gauge formation pressure(psi)
$P_{sg2}$ is the probe 20 strain gauge formation pressure(psi)
$P_{qg3}$ is the probe 19 quartz gauge formation pressure(psi)
$P_{sg3}$ is the probe 19 strain gauge formation pressure(psi)
$P_{qg4}$ is the probe 21 quartz gauge formation pressure(psi)
$P_{sg4}$ is the probe 21 strain gauge formation pressure(psi)

TABLE 1

Summary of Gradient Measurements

| Pressure Measurments (psi) | Probe Spacing (ft) | Flowline Gradient Monitoring (psi/ft) | Formation Gradient (psi/ft) |
|---|---|---|---|
| $\Delta P_1 = P_{qg1} - P_{qg3}$ | $L_5$ | $\rho_{fl1} = \dfrac{P_{qg1} - P_{sg1}}{L_5 \cos(\theta_d)}$ | $\rho_{f1} = \rho_{fl1} - \dfrac{\Delta P_1}{L_5 \cos(\theta_d)}$ |
| $\Delta P_2 = P_{qg2} - P_{qg3}$ | $L_5 - L_6$ | $\rho_{fl2} = \dfrac{P_{qg2} - P_{sg2}}{(L_5 - L_6)\cos(\theta_d)}$ | $\rho_{f2} = \rho_{fl2} - \dfrac{\Delta P_2}{(L_5 - L_6)\cos(\theta_d)}$ |

TABLE 1-continued

Summary of Gradient Measurements

| Pressure Measurments (psi) | Probe Spacing (ft) | Flowline Gradient Monitoring (psi/ft) | Formation Gradient (psi/ft) |
|---|---|---|---|
| $\Delta P_3 = P_{qg1} - P_{qg4}$ | $L_5 + L_6$ | $\rho_{fl3} = \dfrac{P_{qg3} - P_{sg3}}{(L_5 + L_6)\cos(\theta_d)}$ | $\rho_{f3} = \rho_{fl3} - \dfrac{\Delta P_3}{(L_5 + L_6)\cos(\theta_d)}$ |
| $\Delta P_4 = P_{qg2} - P_{qg4}$ | $L_5$ | $\rho_{fl4} = \dfrac{P_{qg4} - P_{sg4}}{L_5\cos(\theta_d)}$ | $\rho_{f4} = \rho_{fl4} - \dfrac{\Delta P_4}{L_5\cos(\theta_d)}$ |
| $\Delta P_5 = P_{sg1} - P_{sg3}$ | $L_5$ | $\rho_{fl1}$ from $\Delta P_1$ | $\rho_{f5} = \rho_{fl1} - \dfrac{\Delta P_5}{L_5\cos(\theta_d)}$ |
| $\Delta P_6 = P_{sg2} - P_{sg3}$ | $L_5 - L_6$ | $\rho_{fl2}$ from $\Delta P_2$ | $\rho_{f6} = \rho_{fl2} - \dfrac{\Delta P_6}{(L_5 - L_6)\cos(\theta_d)}$ |
| $\Delta P_7 = P_{sg1} - P_{sg4}$ | $L_5 + L_6$ | $\rho_{fl3}$ from $\Delta P_3$ | $\rho_{f7} = \rho_{fl3} - \dfrac{\Delta P_7}{(L_5 + L_6)\cos(\theta_d)}$ |
| $\Delta P_8 = P_{sg2} - P_{sg4}$ | $L_5$ | $\rho_{fl4}$ from $\Delta P_4$ | $\rho_{f8} = \rho_{fl4} - \dfrac{\Delta P_8}{L_5\cos(\theta_d)}$ |

Now the mean formation gradient and the standard deviation for all of the measurements can be determined as follows:

$$\rho_f = \frac{\sum \rho_{f(i)}}{n} \text{ is the mean pressure gradient (ps/fti)} \quad (12)$$

$$\sigma(\rho_f) = \sqrt{\frac{n\sum \rho_{f(i)}^2 - (\sum \rho_{f(i)})^2}{n(n-1)}} \text{ is the standard deviation (psi/ft).} \quad (13)$$

The embodiments set forth herein are merely illustrative and do not limit the scope of the invention or the details therein. It will be appreciated that many other modifications and improvements to the disclosure herein may be made without departing from the scope of the invention or the inventive concepts herein disclosed. Because many varying and different embodiments may be made within the scope of the present inventive concept, including equivalent structures or materials hereafter thought of, and because many modifications may be made in the embodiments herein detailed in accordance with the descriptive requirements of the law, it is to be understood that the details herein are to be interpreted as illustrative and not in a limiting sense.

What is claimed is:

1. A method for determining a formation fluid density gradient comprising:
   disposing a multi-probed formation testing tool in a wellbore;
   determining a wellbore fluid density gradient;
   determining a flowline fluid density gradient as a function of the wellbore fluid gradient; and
   determining a formation fluid density gradient as a function of the flowline fluid density gradient.

2. The method of claim 1 wherein the wellbore fluid density gradient is calculated based on a known density of a known fluid in the wellbore.

3. The method of claim 1 wherein determining the wellbore fluid density gradient further comprises:
   measuring a first pressure in the wellbore at a first depth;
   measuring a second pressure in the wellbore at a second depth; and
   calculating the wellbore fluid density gradient using the first and second measured pressures and the difference between the first and second depths.

4. The method of claim 3 wherein the wellbore fluid density gradient is calculated by dividing the difference between the first and second measured pressures by the difference between the first and second depths.

5. The method of claim 1 wherein the flowline fluid density gradient is equal to the wellbore fluid density gradient.

6. The method of claim 1 wherein determining the flowline fluid density gradient further comprises:
   measuring a first pressure in the wellbore through a first port in fluid communication with a first end of the flowline;
   measuring a second pressure in the wellbore through a second port in fluid communication with a second end of the flowline; and
   calculating the flowline fluid density gradient as a function of the first and second measured pressures and the wellbore fluid density gradient.

7. The method of claim 1 wherein determining the formation fluid density gradient further comprises:
   measuring a first formation pressure through a first probe in fluid communication with a first end of the flowline;
   measuring a second formation pressure through a second probe in fluid communication with a second end of the flowline; and
   calculating the formation fluid density gradient as a function of the first and second formation pressures and the flowline fluid density gradient.

8. The method of claim 1 further comprising:
   calibrating a plurality of strain gauges using the flowline fluid density gradient, wherein the strain gauges are used to measure formation pressure; and
   using the strain gauges to monitor changes in the flowline fluid density gradient.

9. A method for operating a multi-probed formation testing tool comprising:
   disposing the multi-probed formation testing tool in a wellbore formed in a formation;
   determining a wellbore fluid density gradient;
   using the wellbore fluid density gradient to determine a flowline fluid density gradient;
   measuring a formation fluid density gradient; and
   using the flowline fluid density gradient to correct the measurement of the formation fluid density gradient.

10. The method of claim 9 wherein the formation testing tool comprises:
   an upper section having a first extendable probe and a first port;
   a lower section having a second extendable probe and a second port;
   a flowline providing fluid communication between the upper and lower sections; and
   a first pressure gauge in communication with the flowline.

11. The method of claim 10 wherein determining the wellbore fluid density gradient further comprises:
   providing isolated fluid communication between the first port and the first pressure gauge at a first depth in the wellbore;
   measuring a first pressure with the first pressure gauge;
   providing isolated fluid communication between the first port and the first pressure gauge at a second depth in the wellbore;
   measuring a second pressure with the first pressure gauge; and
   calculating the wellbore fluid density gradient by dividing the difference between the first and second pressures by the difference between the first and second depths.

12. The method of claim 10 wherein determining the flowline fluid density gradient further comprises:
   providing isolated fluid communication between the first port and the first pressure gauge at a first depth;
   measuring a first pressure with the first pressure gauge;
   providing isolated fluid communication between the second port and the first pressure gauge at a first depth;
   measuring a second pressure with the first pressure gauge; and
   calculating the flowline fluid density gradient as a function of the first and second measured pressures and the wellbore fluid density gradient.

13. The method of claim 10 wherein determining the formation fluid density gradient further comprises:
   extending the first probe into fluid communication with the formation;
   providing isolated fluid communication between the first probe and the first pressure gauge at a first depth;
   measuring a first pressure with the first pressure gauge;
   extending the second probe into fluid communication with the formation;
   providing isolated fluid communication between the second probe and the first pressure gauge at a first depth;
   measuring a second pressure with the first pressure gauge; and
   calculating the formation fluid density gradient as a function of the first and second formation pressures and the flowline fluid density gradient.

14. The method of claim 10 wherein the formation testing tool further comprises a plurality of strain gauges, wherein both the first and second probes are in fluid communication with a dedicated strain gauge.

15. The method of claim 14 further comprising:
   calibrating the plurality of strain gauges using the flowline fluid density gradient;
   using the strain gauges to measure the pressure at each of the probes; and
   using the strain gauges to monitor changes in the flowline fluid density gradient.

16. A method for correcting a formation gradient determined by formation pressure measurements made by a first and second probe of a multi-probe formation testing toll, the method comprising:
   determining a flowline density gradient in a flowline having a length approximately equal to the distance between the first and second probes of the multi-probed formation testing tool;
   determining a formation gradient; and
   using the flowline density gradient to correct the determined formation gradient.

17. The method of claim 16 wherein the determination of the flowline density gradient further comprises:
   measuring a first pressure through a first port in fluid communication with a first end of the flowline;
   measuring a second pressure through a second port in fluid communication with a second end of the flowline; and
   calculating the flowline fluid density gradient as a function of the first and second measured pressures and the distance between the first and second ports, wherein the distance between the first and second ports is approximately equal to the distance between the first and second probes.

18. The method of claim 16 wherein the flowline density gradient is dependent on a wellbore fluid density gradient.

19. The method of claim 16 wherein the determination of the formation gradient further comprises:
   calibrating a strain gauge using the flowline fluid density gradient;
   extending a probe into fluid communication with the formation;
   using the strain gauge to measure the pressure at the probe; and
   using the strain gauges to monitor changes in the flowline fluid density gradient.

20. A formation testing tool comprising:
   an upper section having a first extendable probe and a first port;
   a lower section having a second extendable probe and a second port;
   a flowline providing fluid communication between the upper and lower sections; and
   a first pressure gauge in communication with the flowline, wherein the formation testing tool has a first wellbore pressure measurement mode where said first pressure gauge is in isolated fluid communication with the first port, a second wellbore pressure measurement mode where said first pressure gauge is in isolated fluid communication with the second port, a first formation pressure measurement mode where said first pressure gauge is in isolated fluid communication with the first extendable probe, and a second formation fluid pressure measurement mode where said first pressure gauge is in isolated fluid communication with the second extendable probe.

21. The formation testing tool of claim 20 wherein a wellbore fluid density gradient can be determined using wellbore pressures measured when the tool is in the first and second wellbore pressure measurement modes and a vertical distance between the first and second ports.

22. The formation testing tool of claim 20 wherein a formation fluid density gradient can be determined using formation pressures measured when the tool is in the first and second formation pressure measurement modes and a vertical distance between the first and second extendable probes.

23. The formation testing tool of claim 20 further comprising:
    a first strain gauge in fluid communication with the first extendable probe; and
    a second strain gauge in fluid communication with the second extendable probe.

* * * * *